(12) United States Patent
Zou et al.

(10) Patent No.: US 8,965,095 B2
(45) Date of Patent: Feb. 24, 2015

(54) NOISE BALANCE PRE-RECONSTRUCTION DATA DECOMPOSITION IN SPECTRAL CT

(71) Applicants: Kabushiki Kaisha Toshiba, Tokyo (JP); Toshiba Medical Systems Corporation, Otawara-shi, Tochigi-Ken (JP)

(72) Inventors: Yu Zou, Naperville, IL (US); Xiaolan Wang, Buffalo Grove, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 84 days.

(21) Appl. No.: 13/906,110

(22) Filed: May 30, 2013

(65) Prior Publication Data

US 2014/0355853 A1   Dec. 4, 2014

(51) Int. Cl.
*G06K 9/00* (2006.01)
*G06T 7/00* (2006.01)

(52) U.S. Cl.
CPC .................................. *G06T 7/0012* (2013.01)
USPC ............................................. 382/131; 378/4

(58) Field of Classification Search
USPC ......... 382/100, 128, 131, 132, 168–172, 274, 382/275; 128/922; 378/4–27, 54; 356/303
See application file for complete search history.

(56) References Cited

U.S. PATENT DOCUMENTS 6,721,387 B1 *   4/2004   Naidu et al. ...................... 378/8
7,209,536 B2 *   4/2007   Walter et al. ...................... 378/5

(Continued)

FOREIGN PATENT DOCUMENTS

JP   2006-101926 A   4/2006
JP   2010-500119 A   1/2010

(Continued)

OTHER PUBLICATIONS

International Search Report and International Preliminary Report on Patentability(both in Japanese) corresponding to International Application No. PCT/JP2014/064490 mailed on Sep. 2, 2014.

*Primary Examiner* — Anand Bhatnagar
(74) *Attorney, Agent, or Firm* — Yoshida & Associates, LLC

(57) ABSTRACT

More than two acquired energy or spectral M bins are used for photon counting detectors in a CT system. In the pre-reconstruction data decomposition, the measured photo counts in the M acquired spectral bines are combined into a predetermined fewer number of processed or weighted spectral bines N, which is at least two in number and represents a number of selected basic materials. Since the N basis materials are selected in the imaged subject where N<M, the noise is balanced in the pre-reconstruction data decomposition. In some more detail, after the photon counts n(E) is acquired in each of the M spectral bins as indicated by E=1 to M at each of the detector units for every view, the M acquired spectral bins is combined into the N processed spectral bins so that the photon counts in the N processed spectral bins are substantially balanced to have a least number of differences among the N processed spectral bins. Subsequently, the substantially balanced photon counts in each of the processed spectral bins are related to the material thickness L(i), where i=1 to M. Using a coordinate pursuit technique, the non-zero L(i) is found. The above is repeated for each of the detector units and for all views before reconstructing images based upon the non-zero thickness.

20 Claims, 4 Drawing Sheets

(56) References Cited

U.S. PATENT DOCUMENTS

| | | | |
|---|---|---|---|
| 7,599,465 B2 * | 10/2009 | Walter et al. | 378/4 |
| 8,194,820 B2 * | 6/2012 | Wang et al. | 378/53 |
| 8,378,310 B2 * | 2/2013 | Bornefalk et al. | 250/370.09 |
| 8,787,519 B2 * | 7/2014 | Fan et al. | 378/5 |
| 2006/0109949 A1 * | 5/2006 | Tkaczyk et al. | 378/4 |
| 2009/0060119 A1 * | 3/2009 | Jupiter et al. | 378/2 |
| 2010/0020922 A1 | 1/2010 | Carmi | |
| 2010/0027743 A1 * | 2/2010 | Engel et al. | 378/62 |
| 2010/0202584 A1 * | 8/2010 | Wang et al. | 378/53 |
| 2010/0215230 A1 * | 8/2010 | Bornefalk et al. | 382/128 |
| 2011/0073763 A1 * | 3/2011 | Subbarao | 250/362 |
| 2013/0223587 A1 | 8/2013 | Moriyasu | |

FOREIGN PATENT DOCUMENTS

| | | |
|---|---|---|
| JP | 2011-85479 A | 4/2011 |
| JP | 2013-56149 A | 3/2013 |

* cited by examiner

| $W_1^L$ | 1 | $W_1^H$ | 0 |
| $W_2^L$ | 0.8 | $W_2^H$ | 0.1 |
| $W_3^L$ | 0.1 | $W_3^H$ | 0.8 |
| $W_4^L$ | 0 | $W_4^H$ | 1 |

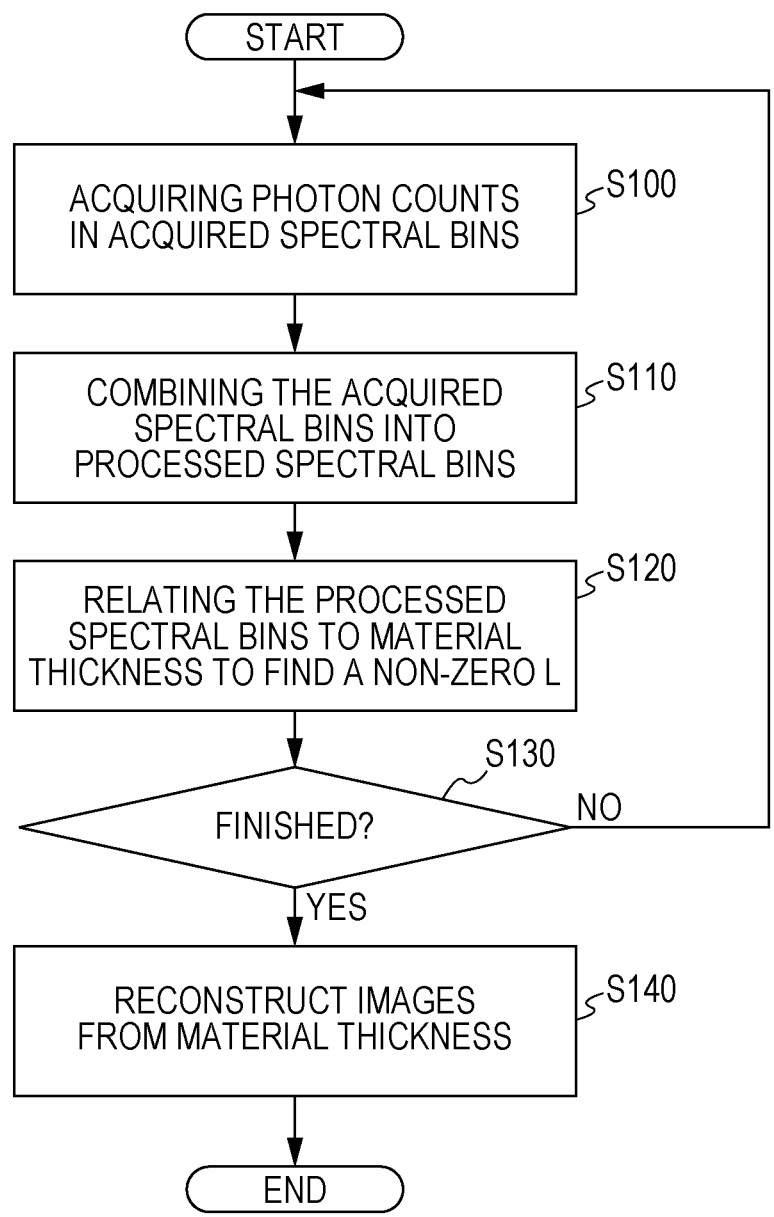

NOISE BALANCE PRE-RECONSTRUCTION DATA DECOMPOSITION IN SPECTRAL CT

FIELD OF THE INVENTION

The embodiments of the current invention are generally related to spectral computed tomography (CT) and more particularly related to a particular manner of weighting for improving noise in the acquired data before reconstructing an image.

BACKGROUND OF THE INVENTION

The dual energy x-ray CT scan data are acquired at two energy levels. For example, the tube is set at the low and high energy levels of 80 kV and 120 kV. Dual source CT-scanners is equipped with two X-ray sources, and each runs at a different energy level for generating the two data sets. On the other hand, in a sandwich detector, the upper layer records the low energy data while the lower layer records the high energy data. To use the dual energy data for material separation, the projection data undergo preconstruction decomposition.

More generally, spectral information is obtained at more than two energy levels for certain x-ray CT scanners. For example, a predetermined number of N energy thresholds is determined according to an average material thickness or the in-air scan, and the basis material thickness is calculated directly based on the N sets of measurement data. In this regard, all detector units and projection views share the same threshold settings. In reality, it is desirable to alter the threshold level between certain views as the spectral changes.

As the spectra change during the scan, the photon counting bins should also accordingly change to maintain a low noise level in the acquired data. Although it may be theoretically possible to dynamically change the thresholds between views, it is technically challenging due to the very short duration of a CT scan. As limited by the current photon counting detector technology, the threshold values may not be properly adapted in the short duration between the views as used in one exemplary rate at 1800 views/0.5 seconds. In general, because read out electronics as well as the detectors have a finite response time and a dead time, the threshold varying implementation under the above requirements is limited given the currently available technology.

Due to the highly non-uniform object composition or thickness, the use of bow-tie filter is also difficult. A bow-tie filter faces difficulty in matching itself with patient geometry, different detector units and views. Furthermore, different units and views are subject to significantly varying attenuations and incident x-ray spectra on detectors.

Consequently, the current use of a universally constant threshold results in undesirable noise balance in a substantially large number of the acquired data sets. The unbalanced noise in the acquired data sets potentially causes severe artifacts in the spectral images. With additional energy bins, the photon numbers in low and or high energy bins should be better balanced.

For these and other reasons, the above described prior art technique remains desired in substantially improving noise balance in the images reconstructed from acquired data including the spectral information.

BRIEF DESCRIPTION OF THE DRAWINGS

FIG. 3 is a flow chart illustrating steps or acts involved in the process of improving noise balance in spectral computed tomography using photon counting detectors according to the current invention.

DETAILED DESCRIPTION OF EMBODIMENT(S)

Figure 1:
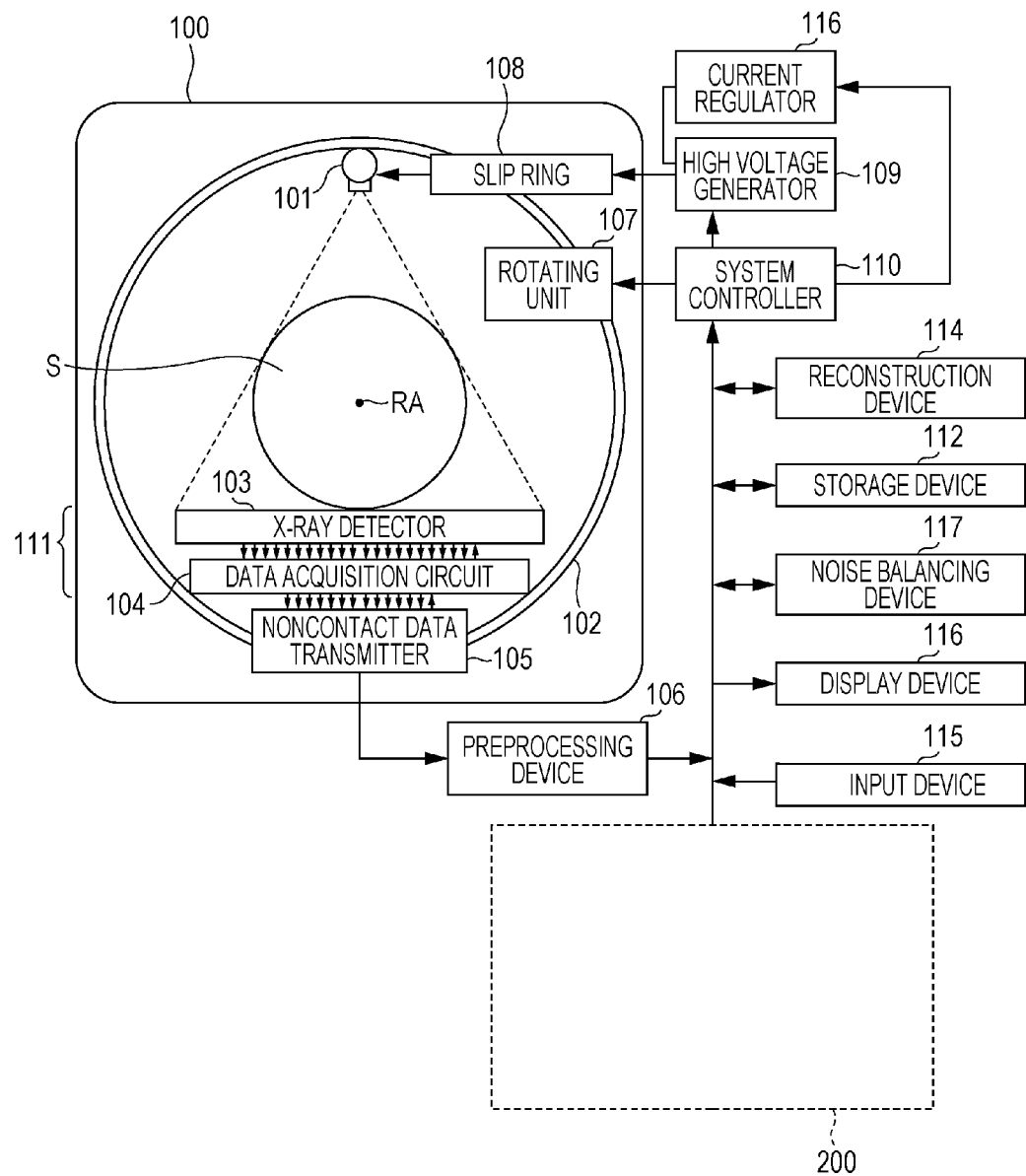
FIG. 1 is a diagram illustrating one embodiment of the multi-slice X-ray CT apparatus or scanner according to the current invention including a gantry 100 and other devices or units.

Referring now to the drawings, wherein like reference numerals designate corresponding structures throughout the views, and referring in particular to FIG. 1, a diagram illustrates one embodiment of the multi-slice X-ray CT apparatus or scanner according to the current invention including a gantry 100 and other devices or units. The gantry 100 is illustrated from a front view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which rotates around axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that applies a tube voltage to the X-ray tube 101 so that the X-ray tube 101 generates X ray. In one embodiment, the high voltage generator 109 is mounted on the frame 102. The X rays are emitted towards the subject S, whose cross sectional area is represented by a circle. The X-ray detector 103 is located at an opposite side from the X-ray tube 101 across the subject S for detecting the emitted X rays that have transmitted through the subject S.

Still referring to FIG. 1, the X-ray CT apparatus or scanner further includes a data acquisition device 111 for detecting the emitted X rays and processing the detected signals. In one embodiment, the X-ray detector 103 is implemented using photon counting detectors for counting photons in each of a predetermined number of energy bins. Each of the energy bins defines a predetermined range of energy in the transmitted X-ray at the detector 103. After detecting the emitted X rays at the X-ray detector 103, a data acquisition circuit 104 converts a signal output from the X-ray detector 103 for each channel into a voltage signal, amplifies it, and further converts it into a digital signal. The X-ray detector 103 and the data acquisition circuit 104 are configured to handle a predetermined total number of projections per rotation (TPPR).

The above described data is sent to a preprocessing device 106, which is housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, display device 116, input device 115, and the scan plan support apparatus 200. The scan plan support apparatus 200 includes a function for supporting an imaging technician to develop a scan plan.

According to one aspect of the current invention, one embodiment of the reconstruction device 114 reconstructs an image from the projection data that is stored in the storage device 112 based upon a filtered backprojection (FBP) technique with noise weighting. In the above embodiment, the reconstruction device 114 reconstructs an image from the projection data based upon a filtered backprojection (FBP) technique with an additional feature of emulating a specific iteration result at a predetermined number of iterations according to a predetermined iterative reconstruction algorithm. The reconstruction device 114 is implemented in a combination of software and hardware and is not limited to a particular implementation. In the following description of the reconstruction device 114, the term, "unit" or "device" is inclusive of hardware and or software. Furthermore, the concept of the reconstruction device 114 is applicable to other modalities including nuclear medicine and magnetic resonance imaging (MRI).

A noise balancing or balance device 117 is implemented on software, hardware or a combination of both for balancing noise in the acquired data by substantially equalizing a number of photon counts among a predetermined number of bins in one embodiment according to the current invention. In general, the noise balance device 117 generally assumes that there are a predetermined number M, which is at least three (M>2) energy bins in each of the photon counting detectors in a CT system and that there are a predetermined number of N basis materials in the imaged subject, where the M energy bins is larger than the N basis materials (M>N). Although it is theoretically possible to have the same number of the energy bins and the basis materials (M=N), the noise balance device 117 requires that the M energy bins is larger than the N basis materials (M>N) in order improve noise balance. After obtaining the photon counts n(E) in each of the M energy bins indicated by E=1 to M at every one of the detector unit 103, the noise balance device 117 combines the M energy bins into the N energy bins so that a number of the photon counts in each of the N bins is substantially equal or as equal as possible or optimal. That is, a number of the photon counts is ideally the same among the M energy bins in the acquired data for each view and each detector unit. The noise balance device 117 subsequently relates the photon counts in each of the substantially, balanced energy bins to the material thickness L(i), where i=1 to N by using a predetermined method such as coordinate pursuit technique to find the non-zero L(i). The noise balance device 117 repeats the above operation for each of the detector elements and each of the views. Finally, images such as monochromatic images are reconstructed according to the material thickness L(i) that the noise balance device 117 has determined.

The material decomposition is performed on the basis of a ray-sum pair in the embodiments according to the current invention. The pairs are spatially and temporally identical in photon counting. The ray-sum pairs are applicable to a dual energy source in one embodiment. In other embodiments according to the current invention, ray-sum trios or higher multiples are applicable for multi-energy CT or spectral CT. In general, a number of the M energy bins corresponds to a number of ray-sums that are generated with M effective spectra along the same ray path. Noise is balanced by combining the M energy bins into the N bins so that a number of the photon counts in each of the N bins is substantially equal or as equal as possible or optimal where M>N. In the process of combining, certain weights are utilized to make the photon counts substantially equal among the N bins, and the weights are related to both a material basis n=1 to N as well as a spectrum m=1 to M. Although it is theoretically possible to have the same number of the energy bins and the basis materials (M=N), the noise balance device 117 requires that the M energy bins is larger than the N basis materials (M>N) in order improve noise balance. That is, a process of the noise balance method or an embodiment of the noise balance device fail to improve noise balance in the dual energy CT data because at least one redundant measurement in a ray path is required.

Figures 2A, 2B:
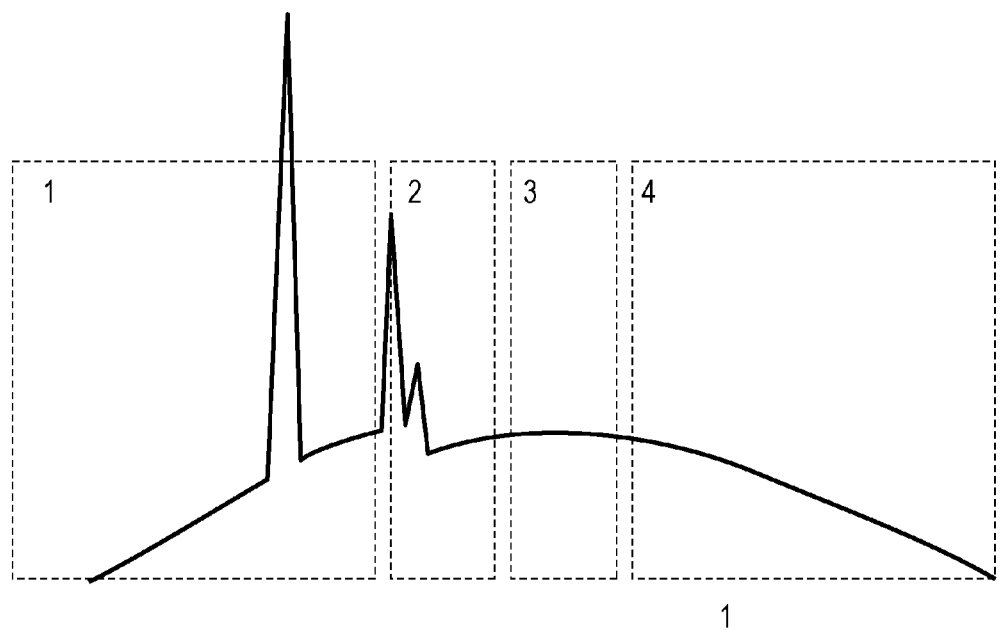
FIG. 2A is a diagram illustrating one embodiment of the noise balance device for improving noise balance according to the current invention.
FIG. 2B is an exemplary set of weight values to be utilized an embodiment of the noise balancing process or device according to the current invention.

Now referring to FIG. 2A, a diagram illustrates that one embodiment of the noise balance device improve noise balance according to the current invention. The diagram includes a simple scheme where a set of photon counts is acquired in a total of four energy bins 1 through 4. In other words, at least three acquired spectral bins are defined according to fixed thresholds so as to acquire the photon counts for a predetermined number of views each having a family of ray-sums. In the spectral data including a set of photon counts in the four acquired spectral bins are obtained. In order to balance the photon counts in the acquired spectral bins, the photon counts are combined or redistributed among another predetermined number of two or more processed spectral bins according to a set of weights that are related to a basis material in the subject and an energy spectrum. In the illustration, a number of the acquired spectral bins is four (M=4) while a number of the processed spectral bins is two (N=2). In the illustrated example, the photon counts are combined from the acquired bins to the processed low-energy and high-energy bins.

Now referring to FIG. 2B, an exemplary set of weight values are illustrated for an embodiment of the noise balancing process according to the current invention. Based upon the above simplified example as illustrated in FIG. 2A, the left side lists a set of four exemplary weight values, each of which is associated with a particular combination of a basis material in the subject and an energy spectrum. In this case, the superscript L indicates the low-energy bin as the processed spectral bins and the subscript indicates one of the acquired spectral bins. By the same token, the right side lists a set of four exemplary weight values, each of which is associated with a particular combination of a basis material in the subject and an energy spectrum. In this case, the processed spectral bin is associated the high-energy bin. In this case, the superscript H indicates the high-energy bin as the processed spectral bins and the subscript indicates one of the acquired spectral bins.

Still referring to FIG. 2A, the weight values are merely illustrative and exemplary. A weight value of 1 generally does not change the photon counts in a particular bin. On the other hand, a value less than 1 changes the photon counts in the associated bin. These weight values make the photon counts in the acquired data set to be redistributed to a particular bin or bins.

Now referring to FIG. 3, a flow chart illustrates steps or acts involved in the process of improving noise balance in spectral computed tomography using photon counting detectors according to the current invention. The process of improving noise balance in spectral computed tomography is implemented in a variety of ways including software, hardware and a combination of both. Although the following steps or acts are optionally performed by the units and components of the embodiment according to the current invention as previously described with respect to FIG. 1, the process of improving noise balance in spectral computed tomography using photon counting detectors is not limited to the performance of the particular embodiment according to the current invention Referring specifically to FIG. 3, the photons are counted or detected for each of the bins at a predetermined photon counting detector or unit in a step S100. The photon counting detector includes a predetermined number of detector elements, and each of the detector elements has a predetermined number of acquired spectral bins that are separated by a corresponding number of fixed thresholds in energy level. In one exemplary implementation, the energy threshold levels are predetermined and stored in the read out electronics. The predetermined number of the acquired spectral bins is at least three for improving noise balance. Thus, a first set of photon counts are obtained in the at least three acquired spectral bins for a predetermined number of views each of which has a family of ray-sums.

Still referring to FIG. 3, after the photon counts are obtained in the at least three acquired spectral bins, the photon counts are now combined into a second set of photon counts in processed spectral bins in a step S110 according to the current invention. A number of the processed spectral bins is two or more and is also equal to a number of the basis materials in the subject. The number of the processed spectral bins is smaller than the predetermined number of the acquired spectral bins so as to balance noise in the spectral data among the processed spectral bins. In balancing the noise, a set of predetermined weights are used, and each of the predetermined weight values is uniquely related to a corresponding one of the basis materials(or processed bins) and a corresponding one of the acquired spectral bins.

After the noise balance is performed in the step S110, the photon counts in the processed spectral bins is related to a material thickness for each of the basis materials in a step S120. The photon counts in each of the processed spectral bins are now better noise balanced than before the step S110. In the step S120, the better noise balanced photon counts in each of the processed spectral bins are now related to the material thickness L(i), where i=1 to M. Using a predetermined coordinate pursuit technique, the non-zero L(i) is determined. In a step S130, it is determined as to where or not the steps S100, S110 and S120 are further performed for any remaining one of the detector elements or units for every view. If it is determined in the step S130 that the steps S100, S110 and S120 have not been completed for each of the detector elements or units for every view, the process proceeds back to the step S100 so that the above steps are performed on the remaining ones of the detector elements or units or the views. On the other hand, if it is determined in the step S130 that the steps S100, S110 and S120 have been completed for each of the detector elements or units for every view, the process proceeds to a step S140, where images are reconstructed from the material thickness of each of the basis materials and the noise balanced photon counts in the processed spectral bins.

Assuming that two material bases are used, at least three energy bins are necessary as acquired spectral bins because the third energy bin is involved in balancing the noise between the first and second bins such as a high energy bin and a low energy bin. For example, the count in the third or middle energy bin is added to the low energy bin when the ray path is long and most of the low energy photons are absorbed by the object. On the other hand, for short ray paths, the count in the middle energy bin is added to the high energy bin.

In general, given an arbitrary N basis materials, M acquired spectral energy bins is larger than N processed spectral energy bins. In other words, the photon counts in the M acquired spectral energy bins are combined into the N processed spectral energy bins in order to improve the noise balance among the energy bins. If the M acquired spectral energy bins are equal to the N processed spectral energy bins in their number, the equal number of the bines fails to improve the noise balance. Then, the measured projection data at energy bin $g_m$ is related to an estimate of the thickness $L_n$ of the basis materials by, $$g_m = \sum_{n=1}^{N} L_n \bar{\mu}_{nm} - g_m^{(BH)}(L), m = 1, M$$

where $g_m^{(BH)}$ is a beam hardening term while $\bar{\mu}_{nm}$ is an average attenuation coefficient while i for basis material n and energy spectrum m. A basis material is indexed by n for specifying a particular basis material among 1 to N basis materials. By the same token, an energy spectrum is indexed by specifying a particular energy spectrum among 1 to M energy spectra.

Given a specific ray path, only one material such as soft tissue may exist, and the thickness of other basis materials will be zero. Thus, the thickness of $L_n$ is determined by minimizing the below cost function or optimization.

$$\Lambda(L) = \sum_{n=1}^{N} |L_n|$$

Then, the above optimization is subject to the data condition.

$$\left| g_m + g_m^{(BH)}(L) - \sum_{n=1}^{N} L_n \bar{\mu}_{nm} \right| < \sigma_m, m = 1, M$$

where $\sigma_m$ indicates the noise of the measured projection $g_m$.

Alternatively, the noise balance step is optionally skipped, and $L_n$ is directly determined by minimizing the cost function with additional constrained conditions. In the constrained algorithm, the thickness L of a basis material is determined from the projection data g based upon the inverse of $(\hat{\mu})$ as expressed in Equation (1):

$$L = (\hat{\mu})^{-1} g \tag{1}$$

Subsequently, the cost function is minimized to denoise or balance noise as expressed in Equation (2):

$$L_n \Leftarrow L_n - a \operatorname{sgn}(L_n) \tag{2}$$

Then, the noise is checked by subjecting to the following data condition as expressed in Equation (3):

$$\left| g_m + g_m^{(BH)}(L) - \sum_{n=1}^{N} L_n \bar{\mu}_{nm} \right| < \sigma_m \tag{3}$$

The projection data is updated by using the beam hardening term with the basis material thickness as expressed in Equation (4):

$$g \Leftarrow g + g^{(BH)}(L) \tag{4}$$

The above steps in the constrained algorithm as summarized in the Equations (1) through (4) are repeated for every view.

In an unconstrained algorithm, the cost function is expressed in Equation (5):

$$\Lambda(L) = \sum_{m=1}^{M} \frac{1}{2\sigma_m^2} \left( g_m + g_m^{(BH)}(L) - \sum_{n=1}^{N} L_n \bar{\mu}_{nm} \right)^2 + \beta \sum_{n=1}^{N} |L_n| \quad (5)$$

where β is a positive constant that decides the weight of the penalty term. The thickness L of a basis material is initialized from the projection data g based upon the inverse of $(\hat{\mu})$ $$L = (\hat{\mu})^{-1} g$$

Subsequently, the gradient of the cost function is expressed in Equation (6):

$$\frac{\partial \Lambda(L)}{\partial L_n} = \qquad (6)$$

$$\sum_{m=1}^{M} \frac{1}{\sigma_M^2} \left( g_m + g_m^{(BH)}(L) - \sum_{n=1}^{N} L_n \bar{\mu}_{nm} \right) \left( \frac{\partial g_m^{(BH)}(L)}{\partial L_n} - \bar{\mu}_{nm} \right) + \beta \mathrm{sgn}(L_n)$$

The Equation (6) is approximated as below in Equation (7):

$$\frac{\partial \Lambda(L)}{\partial L_n} \approx \sum_{m=1}^{M} \frac{\bar{\mu}_{nm}}{\sigma_m^2} \left( \sum_{n=1}^{N} L_n \bar{\mu}_{nm} - g_m - g_m^{(BH)}(L) \right) + \beta \mathrm{sgn}(L_n) \quad (7)$$

The basis material thickness is updated by Equation (8):

$$L_n(i) = L_n^{(0)}(i) - \frac{\frac{\partial \Lambda(L^{(0)})}{\partial L_n}}{\Sigma_{n'} \frac{\partial^2 \Lambda(L^{(0)})}{\partial L_n \partial L_{n'}}}$$

where $$\frac{\partial^2 \Lambda(L^{(0)})}{\partial L_n \partial L_{n'}} \approx \sum_{m=1}^{M} \frac{1}{\sigma_m^2} \left[ \left( \frac{\partial g_m^{(BH)}(L^{(0)})}{\partial L_n} - \bar{\mu}_{nm} \right) \left( \frac{\partial g_m^{(BH)}(L^{(0)})}{\partial L_{n'}} - \bar{\mu}_{n'm} \right) \right]$$

or $$\frac{\partial^2 \Lambda(L^{(0)})}{\partial L_n \partial L_{n'}} \approx \sum_{m=1}^{M} \frac{1}{\sigma_m^2} \bar{\mu}_{nm} \bar{\mu}_{n'm}$$

Lastly, the noise is checked by subjecting to the following data condition as expressed in Equation (9):

$$\left| g_m + g_m^{(BH)}(L) - \sum_{n=1}^{N} L_n \bar{\mu}_{nm} \right| < \sigma_m \quad (9)$$

The above steps in the unconstrained algorithm as summarized in the Equations (6) through (9) are repeated for every view.

In the above exemplary processes of denoising according to the current invention, although a certain cost function is used, the process of improving noise balance is not limited to the exemplary cost function according to the current invention. A second cost function is defined in Equation (10) for given measure projection $g_m$:

$$\Lambda = \sum_{m=1}^{M} \frac{1}{\sigma_m^2} \left( g_m + g_m^{BH} - \sum_{n=1}^{N} \bar{\mu}_{mn} L_n \right)^2 \quad (10)$$

where the noise $\sigma_m^2$ for a spectrum m. To find the minimum or optimize the cost function, the dependence on the beam hardening term, $g_m^{BH}$ on $L_n$ is ignored in weight calculation. Thus, the approximated result is expressed in Equation (11) below:

$$\frac{\partial \Lambda}{\partial L_n} = -\sum_{m=1}^{M} \frac{2\bar{\mu}_{mn}}{\sigma_m^2} \left( g_m + g_m^{BH} - \sum_{n'=1}^{N} \bar{\mu}_{mn'} L_{n'} \right) = 0 \quad (11)$$

Where n'=1,N is a second index for the material basis and takes the same value range as n=1,N. n'=1,N is used to simply distinguish the second use of the index.

The weight value w is defined to implement denoising and is determined for each of the corresponding material basis n and energy spectrum m is now defined as below in Equation (12):

$$w_{nm} = K_n \frac{\bar{\mu}_{mn}}{\sigma_m^2} \quad (12)$$

where $k_n$ is a normalization factor for a particular material basis. The normalization factor $k_n$ is defined as below in Equation (13):

$$1/K_n = \sum_{m=1}^{M} \frac{\bar{\mu}_{mn}}{\sigma_m^2} \quad (13)$$

Thus, the weighted version of the measured projection and basis material thickness should have the following relation as expressed in Equation (14):

$$\hat{g}_n + \hat{g}_n^{BH} - \sum_{n'=1}^{N} \hat{\mu}_{nn'} L_{n'} = 0 \quad (14)$$

where $\hat{g}_n$ is a weighed measure projection data for a material basis n based upon all of the measure spectral energy levels as defined in Equation (15) below:

$$\hat{g}_n = \sum_{m=1}^{M} w_{nm} g_m \quad (15)$$

Similarly, $\hat{g}_n^{BH}$ is a weighed beam hardening term for a material basis n based upon all of the measure spectral energy levels as defined in Equation (16) below:

$$\hat{g}_n^{BH} = \sum_{m=1}^{M} w_{nm} g_m^{BH} \qquad (16)$$

Lastly, $\hat{\mu}_{nn'}$ is a weighed average attenuation coefficient for a material basis n based upon all of the measure spectral energy levels as defined in Equation (17) below:

$$\hat{\mu}_{nn'} = \sum_{m=1}^{M} w_{nm} \bar{\mu}_{mn'} \qquad (17)$$

In addition to the above two cost functions, a third cost function is defined to be used in conjunction the process of noise balancing in spectral data according to the current invention. To define the third cost function, Equation (18) below is assumed.

$$g_m + g_m^{BH} - \sum_{n=1}^{N} \bar{\mu}_{mn} L_n = 0 \qquad (18)$$

where the measured projection data $g_m$ is measured at an energy bin m and is related to an estimate of the thickness $L_n$. The basis materials $g_m^{(BH)}$ is a beam hardening term while $\bar{\mu}_{nm}$ is an average attenuation coefficient for basis material n and energy spectrum m. A basis material is indexed by n for specifying a particular basis material among 1 to N basis materials. By the same token, an energy spectrum is indexed by specifying a particular energy spectrum among 1 to M energy spectra.

Furthermore, the weighted version of the measured projection and basis material thickness as expressed in Equation (14) should be applicable to the relation as expressed in Equation (18) based upon the definitions of weights as expressed in Equations (15), (16) and (17). By ignoring the beam hardening term in Equation (14) for the noise estimation in basis thickness, the following approximation is obtained as in Equation (19).

$$\hat{g}_n - \sum_{n'=1}^{N} \hat{\mu}_{nn'} L_{n'} \approx 0 \qquad (19)$$

By defining a variable $\Xi$ that is the inverse of $(\hat{\mu})$ as in the following equation, $$\sum_{n''=1}^{N} \Xi_{nn''} \hat{\mu}_{n''n'} = \delta_{nn'} \qquad (20)$$

Thus, Equation (19) becomes Equation (21) based upon Equations (20) and (15) to indicate the thickness of a material basis n.

$$L_n = \sum_{n'=1}^{N} \Xi_{nn'} \hat{g}_{n'} = \sum_{n'=1}^{N} \Xi_{nn'} \sum_{m=1}^{M} w_{n'm} g_m \qquad (21)$$

By defining a weighted version of the variable $\Xi$ that is the inverse of $(\hat{\mu})$ as follows in Equation (22):

$$\hat{\Xi}_{nm} = \sum_{n'=1}^{N} \Xi_{nn'} w_{n'm} \qquad (22)$$

Variance and covariance of the basis material thickness is now determined as follows in Equation (23):

$$\mathrm{Var}\{L_n L_{\bar{n}}\} = \sum_{m=1}^{M} \hat{\Xi}_{nm} \hat{\Xi}_{\bar{n}m} \sigma_m^2 \qquad (23)$$

Finally, a cost function as weighted noise of material basis thickness is expressed in Equation (24):

$$\Lambda = \sum_{n=1}^{N} \sum_{\bar{n}=1}^{N} \mathrm{Var}\{L_n L_{\bar{n}}\} = \sum_{n=1}^{N} \sum_{\bar{n}=1}^{N} \sum_{m=1}^{M} \hat{\Xi}_{nm} \hat{\Xi}_{\bar{n}m} \sigma_m^2 \qquad (24)$$

To find the optimal weight as indicated below, the above equations may not be solved analytically. A numerical method should be used to find the optimal weights.

$$\frac{\partial \Lambda}{\partial w_{nm}} = 0$$

Figures 4A, 4B:
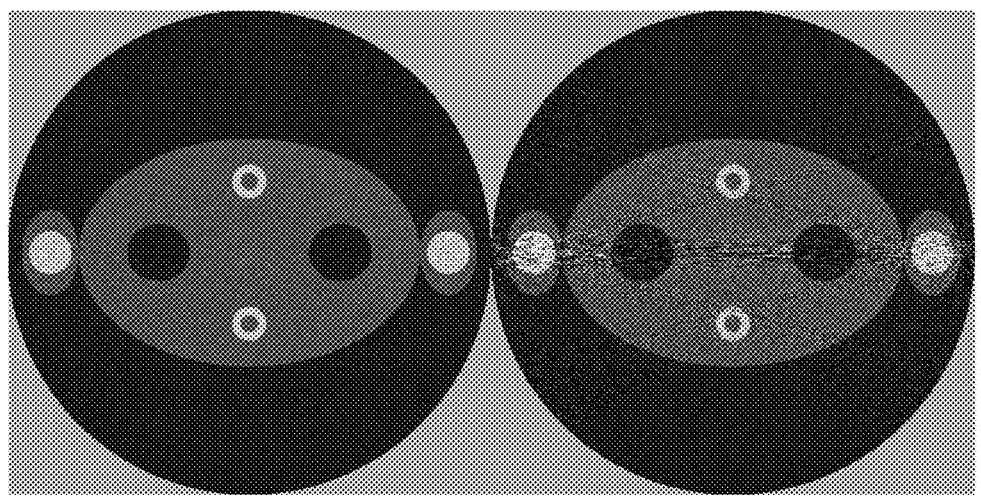
FIG. 4A is a monochromatic image that is reconstructed from the noise balanced data by an embodiment of the process and the apparatus according to the current invention.
FIG. 4B is a monochromatic image that is reconstructed from the data that is not noise balanced by an embodiment of the process and the apparatus according to the current invention.

Now referring to FIGS. 4A and 4B, a pair of images illustrates some effects of noise balance by an embodiment of the process and the apparatus according to the current invention. FIG. 4A is a monochromatic image that is reconstructed from the noise balanced data by an embodiment of the process and the apparatus according to the current invention. FIG. 4B is a monochromatic image that is reconstructed from the data that is not noise balanced by an embodiment of the process and the apparatus according to the current invention. The unbalanced noise has caused severe artifacts in the monochromatic image as shown in FIG. 4B, and the noise likely degrades the diagnostic capability. For this reason, improved noise property likely to increase diagnostic power based upon the eventual image quality.

What is claimed is:

1. A method of noise balancing in spectral data, comprising:

acquiring from a subject spectral data including a first set of photon counts in a first number of at least three acquired spectral bins according to fixed thresholds for a predetermined number of views each having a family of raysums;

combining the first set of the photon counts in the acquired spectral bins into a second set of photon counts in a second number of two or more processed spectral bins according to a third set of weights that are related to one of basis materials in the subject and one of the acquired spectral bins, the second number also being equal to a number of the basis materials and being smaller than the first number so as to balance noise in the spectral data among the processed spectral bins;

relating the photon counts in the processed spectral bins to a material thickness for each of the basis materials; and reconstructing images from the material thickness of each of the basis materials and the processed spectral bins.

2. The method of noise balancing in spectral data according to claim 1 wherein a constrained algorithm is used for relating the photon counts in the processed spectral bins to the material thickness.

3. The method of noise balancing in spectral data according to claim 1 wherein an unconstrained algorithm is used for relating the photon counts in the processed spectral bins to the material thickness.

4. The method of noise balancing in spectral data according to claim 1 wherein acts of the combining and the relating are repeated for each of pairs of the ray-sums in the spectral data as acquired under a duel-energy source.

5. The method of noise balancing in spectral data according to claim 1 wherein acts of the combining and the relating are repeated for each of sets of the ray-sums in the spectral data as acquired under a predetermined polychromatic source.

6. The method of noise balancing in spectral data according to claim 1 wherein the weights are determined by finding a non-zero thickness of a basis material by minimizing a cost function.

7. The method of noise balancing in spectral data according to claim 6 wherein the weights are determined according to a predetermined data condition of:

$$\left| g_m + g_m^{(BH)}(L) - \sum_{n=1}^{N} L_n \bar{\mu}_{nm} \right| < \sigma_m$$

where $g_m$ is measured projection data, $g_m^{(BH)}$ is measured projection data subject to beam hardening according to $\bar{\mu}_{nm}$ is an average attenuation coefficient of a basis material n over a spectral bin m and $L_n$ is material thickness of a basis material $L_n$.

8. The method of noise balancing in spectral data according to claim 6 wherein the cost function is:

$$\Lambda(L) = \sum_{n=1}^{N} |L_n|$$

where $L_n$ is a thickness of a material basis.

9. The method of noise balancing in spectral data according to claim 6 wherein the cost function is:

$$\Lambda = \sum_{m=1}^{M} \frac{1}{\sigma_m^2} \left( g_m + g_m^{BH} - \sum_{n=1}^{N} \bar{\mu}_{mn} L_n \right)^2$$

where $g_m$ is measured projection data, $g_m^{(BH)}$ is measured projection data subject to beam hardening according to $\bar{\mu}_{nm}$ is an average attenuation coefficient of a basis material n over a spectral bin m, $\sigma_m^2$ is noise for a spectrum m and $L_n$ is material thickness of a basis material $L_n$.

10. The method of noise balancing in spectral data according to claim 6 wherein the cost function is:

$$\Lambda = \sum_{n=1}^{N} \sum_{\bar{n}=1}^{N} \mathrm{Var}\{L_n L_{\bar{n}}\} = \sum_{n=1}^{N} \sum_{\bar{n}=1}^{N} \sum_{m=1}^{M} \hat{\Xi}_{nm} \hat{\Xi}_{\bar{n}m} \sigma_m^2$$

where variance and covariance of the basis material thickness $L_n$, $\sigma_m^2$ is noise for a spectrum m, and $\Xi$ is an inverse of a weighed average attenuation coefficient for a material basis n.

11. A system for noise balancing in spectral data, comprising:

a data acquisition device for acquiring from a subject spectral data including a first set of photon counts in a first number of at least three acquired spectral bins according to fixed thresholds for a predetermined number of views each having a family of ray-sums;

a noise balancing device connected to said data acquisition device for combining the first set of the photon counts in the acquired spectral bins into a second set of photon counts in a second number of two or more processed spectral bins according to a third set of weights that are related to one of basis materials in the subject and one of the acquired spectral bins, the second number also being equal to a number of the basis materials and being smaller than the first number so as to balance noise in the spectral data among the processed spectral bins, said noise balancing device relating the photon counts in the processed spectral bins to a material thickness for each of the basis materials; and an image reconstruction device connected to said noise balancing device for reconstructing images from the material thickness of each of the basis materials and the processed spectral bins.

12. The system for noise balancing in spectral data according to claim 11 wherein said noise balancing device utilizes a constrained algorithm for relating the photon counts in the processed spectral bins to the material thickness.

13. The system for noise balancing in spectral data according to claim 11 wherein said noise balancing device utilizes an unconstrained algorithm for relating the photon counts in the processed spectral bins to the material thickness.

14. The system for noise balancing in spectral data according to claim 11 wherein said noise balancing device repeatedly combines and relates for each of pairs of the ray-sums in the spectral data as acquired under a duel-energy source.

15. The system for noise balancing in spectral data according to claim 11 wherein said noise balancing device repeatedly combines and relates for each of sets of the ray-sums in the spectral data as acquired under a predetermined polychromatic source.

16. The system for noise balancing in spectral data according to claim 11 wherein said noise balancing device determines the weights by finding a non-zero thickness of a basis material by minimizing a cost function.

17. The system for noise balancing in spectral data according to claim 16 wherein said noise balancing device determines the weights according to a predetermined data condition of:

$$\left| g_m + g_m^{(BH)}(L) - \sum_{n=1}^{N} L_n \bar{\mu}_{nm} \right| < \sigma_m$$

where $g_m$ is measured projection data, $g_m^{(BH)}$ is measured projection data subject to beam hardening according to $\bar{\mu}_{nm}$ is an average attenuation coefficient of a basis material n over a spectral bin m and $L_n$ is material thickness of a basis material $L_n$.

18. The system for noise balancing in spectral data according to claim 16 wherein the cost function is:

$$\Lambda(L) = \sum_{n=1}^{N} |L_n|$$

where $L_n$ is a thickness of a material basis.

19. The system for noise balancing in spectral data according to claim 16 wherein the cost function is:

$$\Lambda = \sum_{m=1}^{M} \frac{1}{\sigma_m^2} \left( g_m + g_m^{BH} - \sum_{n=1}^{N} \bar{\mu}_{mn} L_n \right)^2$$

where $g_m$ is measured projection data, $g_m^{(BH)}$ is measured projection data subject to beam hardening according to $\bar{\mu}_{nm}$ is an average attenuation coefficient of a basis material n over a spectral bin m, $\sigma_m^2$ noise for a spectrum m and $L_n$ is material thickness of a basis material $L_n$.

20. The system for noise balancing in spectral data according to claim 16 wherein the cost function is:

$$\Lambda = \sum_{n=1}^{N} \sum_{\bar{n}=1}^{N} \mathrm{Var}\{L_n L_{\bar{n}}\} = \sum_{n=1}^{N} \sum_{\bar{n}=1}^{N} \sum_{m=1}^{M} \hat{\Xi}_{nm} \hat{\Xi}_{\bar{n}m} \sigma_m^2$$

where variance and covariance of the basis material thickness $L_n$, $\sigma_m^2$ is noise for a spectrum m, and $\Xi$ is an inverse of a weighed average attenuation coefficient for a material basis n.

* * * * *